United States Patent [19]
Chen

[11] Patent Number: 5,232,458
[45] Date of Patent: Aug. 3, 1993

[54] SAFETY SYRINGE WITH RETRACTABLE SELF-BIASED NEEDLE

[76] Inventor: Long-Hsiung Chen, c/o Hung Hsing Patent Service Center, P.O. Box 55-1670, Taipei (10477), Taiwan

[21] Appl. No.: 952,593

[22] Filed: Sep. 28, 1992

[51] Int. Cl.⁵ ............................................. A61M 5/32
[52] U.S. Cl. ................................... 604/195; 604/110
[58] Field of Search ............... 604/110, 187, 195, 198, 604/192, 218

[56] References Cited
U.S. PATENT DOCUMENTS 4,804,370 2/1989 Haber et al. ....................... 604/195

Primary Examiner—John D. Yasko

[57] ABSTRACT

A safety syringe includes: a hollow needle secured in a front portion of the syringe for injection use having a needle head portion formed on a rear portion of the needle, and a plunger slidably held in the syringe for boosting a liquid medicine in the syringe to be injected into a patient through the hollow needle having a biasing socket recessed in a front portion of the plunger engageable with the needle head portion for biasing the needle obliquely within the syringe when retracting the plunger and the needle into the syringe, thereby preventing an outward protruding of the retracted needle for preventing its injury or infectious contamination to the surroundings.

5 Claims, 4 Drawing Sheets

SAFETY SYRINGE WITH RETRACTABLE SELF-BIASED NEEDLE

BACKGROUND OF THE INVENTION

A conventional syringe after being used for medical injection purpose will be treated for waste disposal. If the injection needle mounted on the syringe is protruded outwardly, it may cause infectious contamination or pollution, hazardous to environmental protection and human health. Even some improvements had been made to automatically retract the injection needle into the syringe body to prevent injury or infectious contamination to someone, the retracted needle as spring tensioned may still be inadvertently protruded outwardly by an external force or protruded downwardly when pendently held or when disposed in a garbage yard for an accidentally protruding of the needle to cause injury to the others.

SUMMARY OF THE INVENTION

The object of the present invention is to provide a syringe of which a needle may be biased after being retracted into the syringe to prevent a re-protrusion of the needle outwardly from the syringe to prevent injury or infectious contamination to the surroundings.

According to the invention, there is provided a safety syringe including: a hollow needle secured in a front portion of the syringe for injection use having a needle head portion formed on a rear portion of the needle, and a plunger slidably held in the syringe for boosting a liquid medicine in the syringe to be injected into a patient through the hollow needle having a biasing socket recessed in a front portion of the plunger engageable with the needle head portion for biasing the needle obliquely within the syringe when retracting the plunger and the needle into the syringe, thereby preventing an outward protruding of the retracted needle for preventing its injury or infectious contamination to the surroundings.

DETAILED DESCRIPTION

Figure 1:
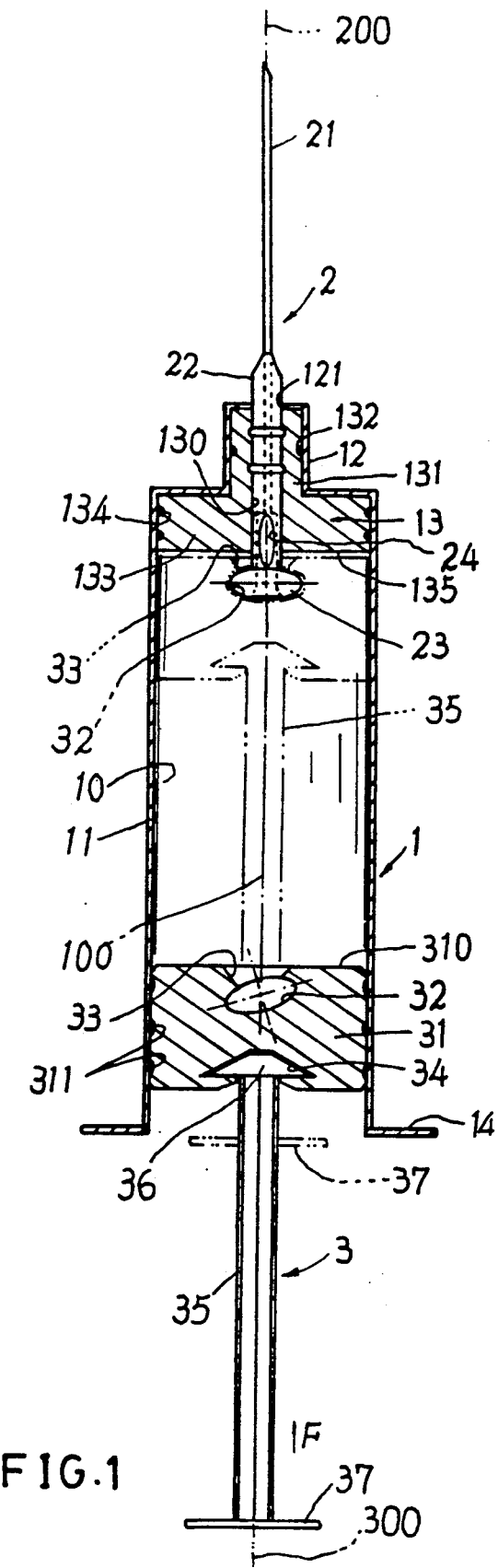
FIG. 1 is an illustration showing the present invention before using.
Figure 3:
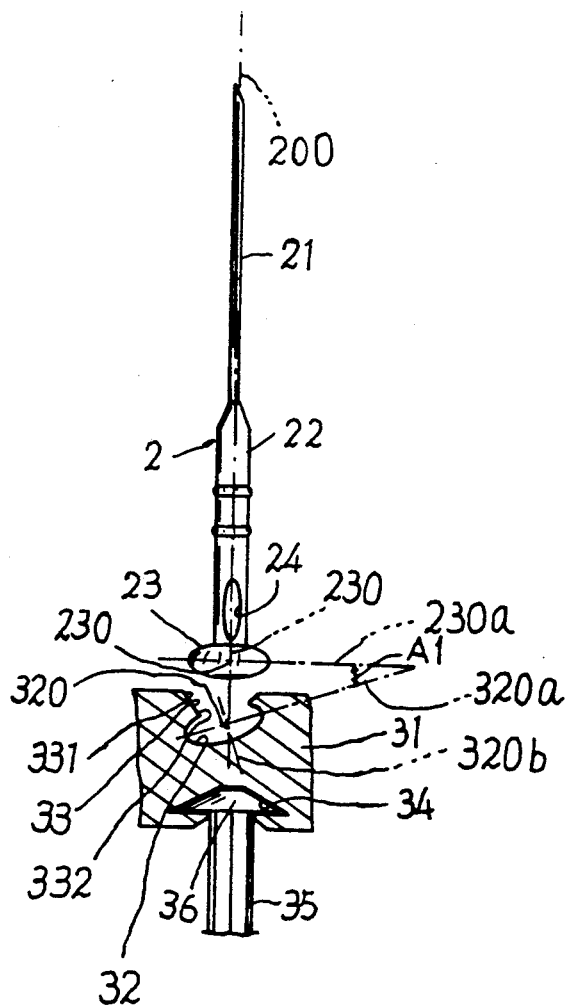
FIG. 3 is an illustration showing a needle intended to be coupled with a plunger of the present invention.
Figure 2:
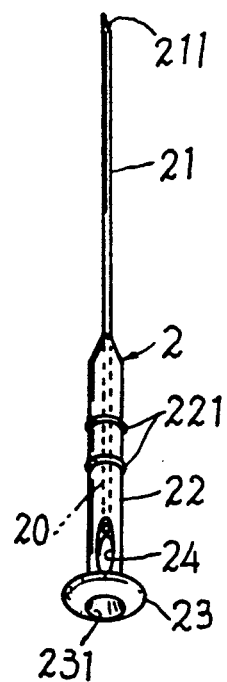
FIG. 2 is a perspective view of a needle device of the present invention.

As shown in FIGS. 1-4, the present invention comprises: a syringe means 1, a needle device 2 mounted in a front portion of the syringe means 1, and a plunger means 3 slidably held in the syringe means 1.

The syringe means 1 includes: a syringe cylinder 11 having a hollow bore portion 10 defined in the syringe cylinder 11 and a syringe axis 100 longitudinally existing in a central portion of the syringe cylinder 11, a sleeve portion 12 formed in a front portion of the cylinder 11 contracted from the cylinder 11 having a needle port 121 formed in a central opening of the sleeve 12, a front plug 13 having a plug tip portion 131 embedded in the sleeve portion 12 and a plug shoulder portion 133 embedded in a front portion of the cylinder 11 connected with the tip portion 131 and a tunnel 130 formed in the plug 13 communicating the needle port 121 for inserting the needle device 2 in the tunnel 130, and a syringe handle 14 formed on a rear end portion of the cylinder 11.

The plug 13 has a plurality of packing rings 132, 134 circumferentially formed on the tip portion 131 and the shoulder portion 133 of the plug 13 for frictionally holding the plug 13 in the syringe means 1 and also for preventing liquid leakage from the cylinder 11.

The needle device 2 includes: a needle portion 21 having a tip end 211, a shank portion 22 connected with the needle portion 21 having a plurality of needle rings 221 circumferentially formed on the shank portion 22 for firmly engaging the shank portion 22 in the tunnel 130 of the syringe means 1 for protruding the needle portion 21 beyond the needle port 121 of the syringe means 1, a needle head portion 23 formed on a rear portion of the shank portion 22 protruding rearwardly beyond a plug surface 135 formed on a rear end surface of the plug 13 to be engageable with a biasing socket 32 of the plunger means 3, a needle hole 20 formed through the needle portion 21, the shank portion 22 and the needle head portion 23 for passing liquid medicine therethrough for injection use, a needle axis 200 longitudinally existing in a central portion of the needle device 2 normally aligned with the syringe axis 100, and at least a venting slot 24 formed in the shank portion 22 adjacent to the needle head portion 23 for venting air outwardly through the needle hole 20 of the needle device 2.

The needle head portion 23 may be formed as elliptic shape having a needle-head center 230 intersected by a transverse head axis 230a and a conjugate head axis 230b perpendicular to the transverse head axis 230a defined in the head portion 23 elliptically shaped, with the conjugate head axis 230b of the needle head portion 23 aligned with the needle axis 200 of the needle device 2 and normally aligned with the syringe axis 100 of the syringe means 1 when the needle device 2 is normally secured on the syringe means 1.

The venting slot 24 formed in the shank portion 22 of the needle device 2 is generally elongate shaped to have a first section of a total length of the slot 24 positioned in the plug 13 and to have a second section of the total length of the slot 24 positioned beyond the plug surface 135 communicating the hollow bore portion 10 in the syringe cylinder 11. Each first section and second section of the total length of the slot 24 may be one half of the total slot length, but not limited in this invention.

The plunger means 3 includes: a plunger 31 reciprocatively held in the syringe cylinder 11, the biasing socket 32 recessed in a front end portion of the plunger 31 operatively obliquely engageable with the needle head portion 23, a guiding port 33 formed in a front portion of the socket 32 converging rearwardly for communicating the socket 32 for slidably guiding the needle head portion 23 rearwardly through the guiding port 33 to be engaged into the socket 32 for biasing the needle portion 21 obliquely when retracting the needle device 2 within the hollow bore portion 10 in the syringe cylinder 11, a plunger rod 35 connected with the plunger 31 and protruding rearwardly to have a plunger-rod handle 37 formed on a rear end portion of the rod 35 for grasping the handle 37 for squeezing the plunger 31 for injection use, and a plunger axis 300 longitudinally existing in a central portion of the plunger 31 and the rod 35. The guiding port 33 includes a front large opening 331 having a size generally equal to that of the needle head portion 23, and a rear small opening 332 contracted from the large opening 331 and communicating the socket 32.

Figure 4:
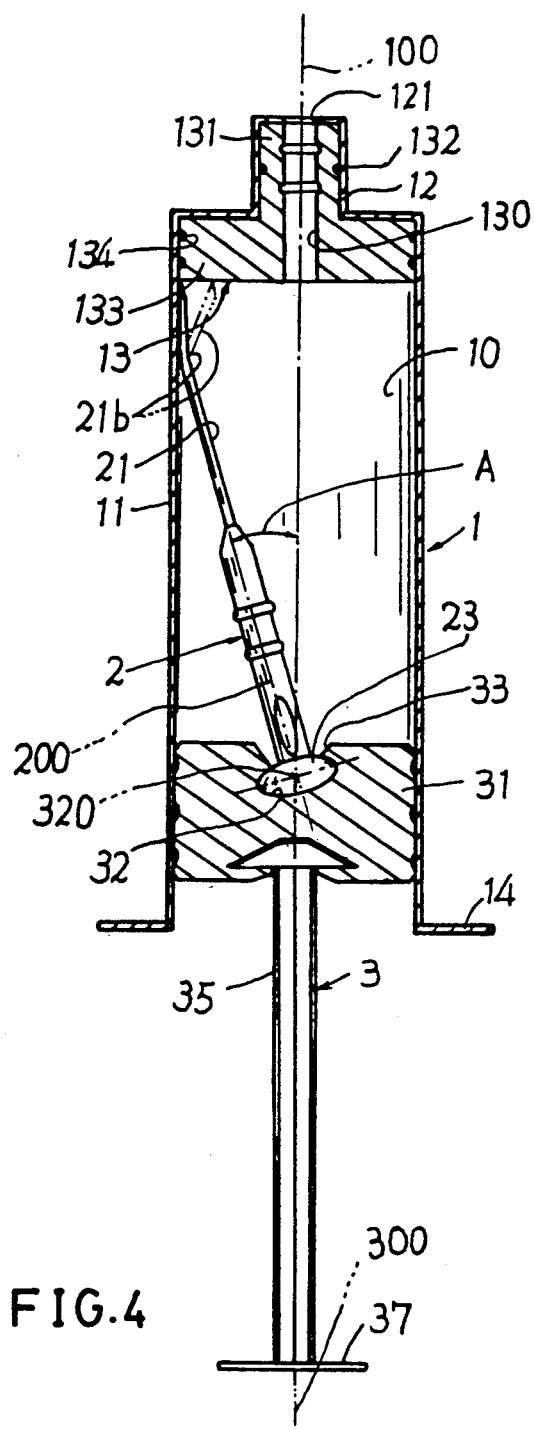
FIG. 4 shows a biased needle retracted in a syringe in accordance with the present invention.
Figure 3A:
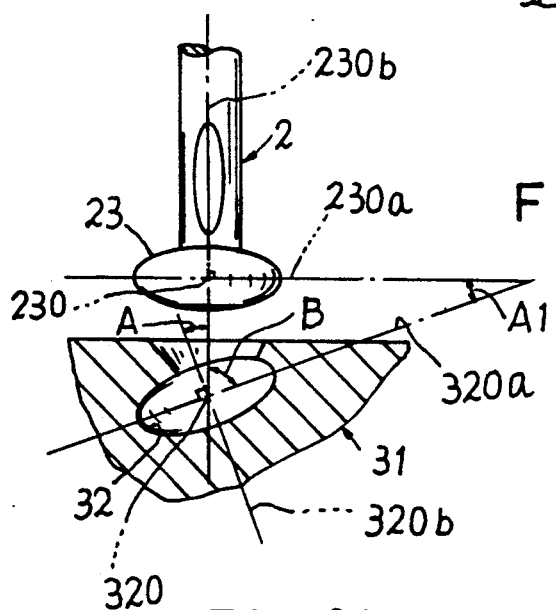
FIG. 3A is a partial enlarged illustration of the needle head portion with the socket of this invention.

The biasing socket 32 of the plunger means 3 may be formed as an elliptic shape having a socket center 320 intersected by a transverse socket axis 320a and a conjugate socket axis 320b perpendicular to the transverse socket axis 320a defined within the socket 32 with the conjugate socket axis 320b normally deviated from the conjugate head axis 230b and the syringe axis 100 of the syringe means 1 for an acute angle A defined between the conjugate socket axis 320b and the syringe axis 100 when retracting the needle device 2 within the hollow bore portion 10 in the syringe cylinder 11 after using the needle for medical injection purpose as shown in FIGS. 4, 3A, with the socket center 320 normally aligned with the needle-head center 230 of the needle device 2 and normally aligned with the syringe axis 100 when the needle device is normally secured on the syringe means, whereby upon a squeezing of the plunger 31 frontwardly by pushing the rod handle 37 frontwardly F (FIG. 1) to boost a liquid medicine (not shown) filled in the cylinder 11 for injection use through the needle hole 20, the needle head portion 23 will be engaged with the socket 32 of the plunger 31 when the plug surface 135 matching with a plunger front surface 310 for "transplanting" the needle head portion 23 into the socket 32 of the plunger 31 (since the plunger 31 is made flexible such as from rubber material, the plunger can be compressed for a snug engagement of the needle portion 23 with the socket 32); and upon a retraction of the plunger 31, the needle device 2 will be retracted into the bore portion 10 of the syringe cylinder 11 and the needle-head portion 23 and the needle portion 21 will be biased with the acute angle A since the conjugate socket axis 320b of the biasing socket 32 is already deviated from the syringe axis 100 with the acute angle A as aforementioned, thereby preventing a re-protrusion of the needle portion 21 outwardly from the syringe cylinder for preventing an injury or infectious contamination to an environmental surroundings.

The plunger 31 may be formed with a plurality of annular rings 311 for resiliently retaining the plunger 31 in the syringe cylinder 11 for smoothly performing the injection operation.

Whenever injecting the needle 2 into a patient's skin, a counter force acting backward by the patient may be overcome by the needle rings 221 and the plunger 31 frictionally held in the syringe cylinder 11, thereby stabilizing the needle 2 for its injecting operation.

The plunger 31 may be formed with a recess 34 in a rear surface of the plunger 31 to be engaged with a coupling member 36 formed on a front end of the rod 35 for connecting the plunger 31 with the rod 35.

As shown in FIG. 4, after retracting the needle 2 in the cylinder 11, a further apply of an external force for protruding the needle portion 21 outwardly, the needle portion 21 as previously biased to a side corner in the cylinder 11 will be bent (numeral 21b) to prevent its outward protrusion.

Therefore, this invention is quite safe for preventing an unexpected inadvertent protruding of an injection needle from the syring after being used, thereby beneficial for medical or hospital waste disposal for enhancing environmental hygiene and human health.

Figure 5:
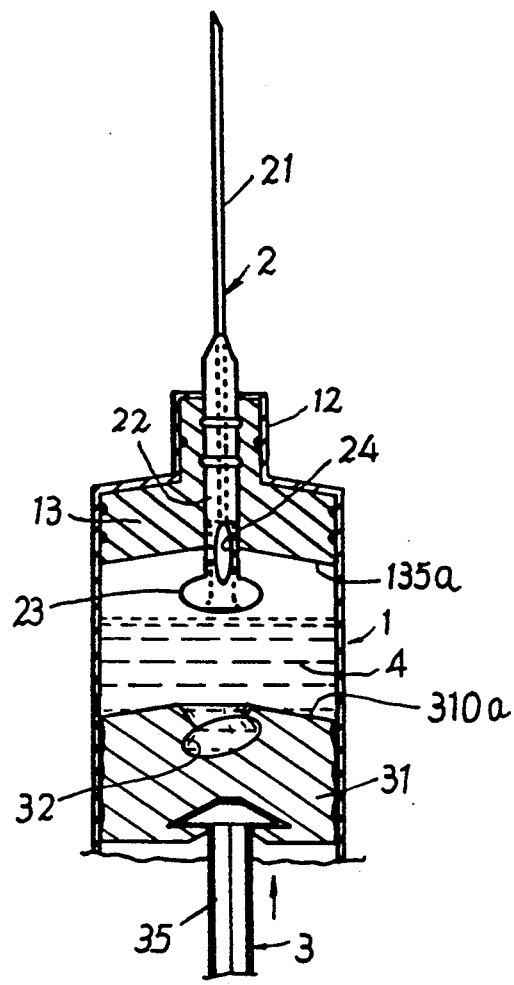
FIG. 5 shows another preferred embodiment of the present invention.

As shown in FIG. 5, the matching surfaces 135a, 310a of the plug 13 and the plunger 31 may be slightly tapered frontwardly to smoothly boosting a liquid medicine 4 frontwardly for an efficient injection purpose.

As shown in FIG. 3A, the two transverse axes 230a, 320a of the needle head portion 23 and the socket 32 also define an acute angle A1 equal to the acute angle A of the biased angle of the retracted needle 2 as shown in FIG. 4, since A1+B=90°, A+B=90°, so that A1=A as illustrated in FIG. 3A.

I claim:

1. A safety syringe comprising: a syringe means for filling liquid medicine therein; a needle device secured in a front portion of the syringe means for injection use having a needle head portion formed on a rear portion of the needle device, and a plunger means slidably held in the syringe means for boosting the liquid medicine in the syringe means to be injected into a patient through the needle device having a biasing socket recessed in a front portion of the plunger means engageable with the needle head portion of said needle device for biasing said needle device obliquely within the syringe means when retracting the plunger means and the needle device into the syringe means, thereby preventing an outward protruding of a retracted needle device for preventing injury or infectious contamination by the needle device to environmental surroundings;

said syringe means including: a syringe cylinder having a hollow bore portion defined in the syringe cylinder and a syringe axis longitudinally existing in a central portion of the syringe cylinder, a sleeve portion formed in a front portion of the cylinder contracted from the cylinder having a needle port formed in a central opening of the sleeve, a front plug having a plug tip portion embedded in the sleeve portion and a plug shoulder portion embedded in a front portion of the cylinder connected with the tip portion and a tunnel formed in the plug communicating the needle port for inserting the needle device in the tunnel and in the needle port, and a syringe handle formed on a rear end portion of the cylinder;

said needle device including: a needle portion, a shank portion connected with the needle portion having a plurality of needle rings circumferentially formed on the shank portion for firmly engaging the shank portion in the tunnel of the syringe means for protruding the needle portion beyond the needle port of the syringe means, the needle head portion formed on a rear portion of the shank portion protruding rearwardly beyond a plug surface formed on a rear end surface of the plug to be engageable with the biasing socket of the plunger means, a needle hole formed through the needle portion, the shank portion and the needle head portion for passing liquid medicine therethrough for injection use, a needle axis longitudinally existing in a central portion of the needle device normally aligned with the syringe axis, and at least a venting slot formed in the shank portion adjacent to the needle head portion for venting air outwardly through the needle hole of the needle device;

and said plunger means including: a plunger reciprocatively held in the syringe cylinder, the biasing socket recessed in a front end portion of the plunger operatively obliquely engageable with the needle head portion, a guiding port formed in a front portion of the socket converging rearwardly for communicating the socket for slidably guiding the needle head portion rearwardly through the guiding port to be engaged into the socket for biasing the needle portion obliquely when retracting the needle device within the hollow bore portion in the syringe cylinder, a plunger rod connected with the plunger and protruding rearwardly to have a plunger-rod handle formed on a rear end portion of the rod for grasping the handle for squeezing the plunger for injection use, and a plunger axis longitudinally existing in a central portion of the plunger and the rod.

2. A safety syringe according to claim 1, wherein said needle head portion is formed as elliptic shape having a needle-head center intersected by a transverse head axis and a conjugate head axis perpendicular to the transverse head axis defined in the needle head portion elliptically shaped, with the conjugate head axis of the needle head portion aligned with the needle axis of the needle device and normally aligned with the syringe axis of the syringe means when the needle device is normally secured on the syringe means.

3. A safety syringe according to claim 1, wherein said venting slot formed in the shank portion of the needle device is generally elongate shaped to have a first section of a total length of the slot positioned in the plug and to have a second section of the total length of the slot positioned beyond the plug surface of said plug communicating the hollow bore portion in the syringe cylinder.

4. A safety syringe according to claim 1, wherein said guiding port of said plunger means includes a front large opening having a size generally equal to that of said needle head portion, and a rear small opening contracted from said front large opening having a size small than that of said needle head portion and communicating the biasing socket.

5. A safety syringe according to claim 1, wherein said biasing socket of the plunger means is formed as an elliptic shape having a socket center intersected by a transverse socket axis and a conjugate socket axis perpendicular to the transverse socket axis defined within the socket, with the conjugate socket axis normally deviated from the conjugate head axis and the syringe axis of the syringe means for an acute angle defined between the conjugate socket axis and the syringe axis when retracting the needle device within the hollow bore portion in the syringe cylinder after using the needle for medical injection purpose, with the socket center normally aligned with the needle-head center of the needle device and normally aligned with the syringe axis when the needle device is normally secured on the syringe means, whereby upon a squeezing of the plunger frontwardly by pushing the rod handle frontwardly to boost a liquid medicine in the cylinder for injection use, the needle head portion will be engaged with the socket of the plunger; and upon a retraction of the plunger, the needle device will be retracted into the bore portion of the syringe cylinder and the needle-head portion and the needle portion will be biased with the acute angle from the syringe axis for preventing a reprotrusion of the needle portion outwardly from the syringe cylinder for preventing an injury and infectious contamination to an environmental surroundings.

* * * * *